(12) United States Patent
Ondrla

(10) Patent No.: US 8,192,497 B2
(45) Date of Patent: *Jun. 5, 2012

(54) JOINT PROSTHESIS HAVING INFINITELY ADJUSTABLE HEAD

(75) Inventor: Jeffrey Michael Ondrla, Leesburg, IN (US)

(73) Assignee: DePuy Products, Inc., Warsaw, IN (US)

( * ) Notice: Subject to any disclaimer, the term of this patent is extended or adjusted under 35 U.S.C. 154(b) by 246 days.

This patent is subject to a terminal disclaimer.

(21) Appl. No.: 12/614,936

(22) Filed: Nov. 9, 2009

(65) Prior Publication Data

US 2010/0057210 A1    Mar. 4, 2010

Related U.S. Application Data

(63) Continuation of application No. 10/610,257, filed on Jun. 30, 2003, now Pat. No. 7,615,080.

(51) Int. Cl.
*A61F 2/40* (2006.01)
(52) U.S. Cl. .................................................. 623/19.14
(58) Field of Classification Search .... 623/19.11–19.14, 623/22.11, 22.4, 22.42–22.46
See application file for complete search history.

(56) References Cited

U.S. PATENT DOCUMENTS

| | | | |
|---|---|---|---|
| 4,565,345 A | 1/1986 | Templeman | |
| 5,358,526 A | 10/1994 | Tornier | |
| 5,702,457 A * | 12/1997 | Walch et al. | 623/19.13 |
| 5,741,335 A | 4/1998 | Gerber et al. | |
| 5,910,171 A * | 6/1999 | Kummer et al. | 623/18.11 |
| 6,203,575 B1 | 3/2001 | Farey | |
| 6,206,925 B1 | 3/2001 | Tornier | |
| 6,228,120 B1 | 5/2001 | Leonard et al. | |
| 6,783,549 B1 | 8/2004 | Stone et al. | |
| 7,615,080 B2 * | 11/2009 | Ondrla | 623/19.11 |
| 2005/0113931 A1 | 5/2005 | Horber | |

FOREIGN PATENT DOCUMENTS

| | | |
|---|---|---|
| DE | 10123517 | 11/2002 |
| EP | 0634154 | 1/1995 |

* cited by examiner

*Primary Examiner* — Pedro Philogene

(74) *Attorney, Agent, or Firm* — Maginot, Moore & Beck

(57) ABSTRACT

A joint prosthesis, as a replacement for a ball and socket type joint, has a head that allows for infinite dialability and/or angular orientation with respect to an implanted stem, particularly during a procedure for implanting the prosthesis. The angular orientation is positionable and fixed or locked in a set position without utilizing external or separate fasteners. An expandable conjoining member associated with the prosthesis stem receives the head and allows for the positioning thereof. The expandable conjoining member is fixed in position through expansion of the expandable conjoining member to produce a friction fit (wedging) of the expandable conjoining member within a receiving socket of the stem. Expansion of the expandable conjoining member is achieved through coupling interaction of a stem of the head with the conjoining member.

7 Claims, 5 Drawing Sheets

JOINT PROSTHESIS HAVING INFINITELY ADJUSTABLE HEAD

This application is a continuation of application Ser. No. 10/610,257, filed on Jun. 30, 2003 (now U.S. Pat. No. 7,615,080 issued Nov. 10, 2009), the disclosure of which is herein totally incorporated by reference in its entirety.

BACKGROUND

1. Field of the Invention

The present invention relates to prosthetic joint devices and, more particularly, to a joint prosthesis having an infinitely variable head.

2. Background Information

The state of the prosthetic joint market has progressed such that a surgeon generally approaches joint replacement surgery in just one of two strategic manners. This is especially true with respect to the prosthetic shoulder market. With respect to a humeral replacement procedure, in one strategic manner a surgeon is provided with instrumentation and technique guidelines for the particular shoulder prosthesis or prosthesis line. The guidelines and/or instrumentation direct or dictate the angle of humeral head resection for the implant (prosthesis). This angle is in relation to the humeral intramedullary (IM) canal and is designed to match an optimum set of angles already present in the prosthesis design.

Another strategic manner is to perform the shoulder replacement surgery in accordance with a patient's anatomy. Particularly, the humeral head is resected according to angles perceived to be "anatomic" in the opinion of the surgeon, not according to angles already present in the prosthesis design. The prosthesis is designed such that the configuration of the prosthesis is intra-operatively adjustable (i.e. adjustable during the surgical implantation thereof). This type of configuration allows the prosthesis to be adjustable such that is can match the surgical boney preparation.

Even with respect to these two divergent manners of surgical strategy, a common problem in shoulder surgery is matching the humeral resection angle to the predetermined angle designed into the prosthesis. This angle may be described as the angle between a prosthetic collar and a diaphyseal section of the stem. In the case of a collarless stem, the angle may describe the difference between a long axis of the stem and an inferior surface of the prosthetic head. It is considered optimal for fixation and biomechanics if the resected angle and the angle of the prosthesis are identical—thereby allowing intimate contact between the superior surface of the resected bone and the inferior surface of the implant.

Moreover, the angular version in which the prosthesis is implanted will have a significant impact on the biomechanics of the prosthetic joint. Currently, most shoulder prosthesis systems on the market dictate the varus/valgus angle of the bone cut. This strategy does not allow the surgeon to easily alter biomechanics after the prosthesis has been trialed, much less implanted.

There are two known products currently marketed that attempt to resolve at least one of the above-noted issues.

A first product currently marketed as a solution to the problems addressed above is the CenterPulse Anatomica based on U.S. Pat. No. 5,741,335 issued to Gerber. This product provides a humeral head that is infinitely adjustable in varus/valgus and anterior/posterior angles relative to the stem portion of the prosthesis. This is accomplished through a spherical shaped protrusion on the superior surface of the stem that fits into a spherical recess in the humeral head. These mating surfaces allow the head to be articulated about the stem, thus allowing adjustable positioning of the head. The head can be locked in a position relative to the stem. This solution provides adjustment of the neck-shaft angle as well as being able to affect adjustment of the version through flexibility in the anterior/posterior angle. The locking means, however, is sub-optimal. Particularly, the locking mechanism, requires the turning of a locking screw that has its head facing lateral and inferior, for which there is no access once the stem has been cemented. This eliminates the ability to adjust head position once the stem has been implanted, and forces a total revision if articular surfaces ever need to be revised. Lastly, the protrusion on the humeral stem even when the humeral head is not in place limits the surgeon's access to the glenoid in preparation for a glenoid replacement.

A second product, the Tornier-Aequalis system (based on U.S. Pat. No. 5,702,457 issued to Tornier) provides a modular junction within the metaphyseal region of the stem which allows a small block between the stem and humeral head to be interchanged. This block is available in multiple angles, thus allowing the surgeon to select the block that best fits the boney anatomy as resected. This system, however, has two primary weaknesses. First, the use of modular blocks obviously forces the design to only allow angular adjustments in finite increments. Second, the need to adjust the angle through modular blocks forces the surgeon to remove the stem, change out a component, and reset the stem. This presents inconvenience, as well as risk for interfering with resected bone and compromising fixation.

A problem with the above-identified and other prosthetic systems, is the need for complicated instrumentation for correctly orienting and/or adjusting the final orientation of the head portion of the prosthesis. Moreover, since fixation for the above-identified and other prosthetic systems is provided by mechanisms that are outside of the humeral stem, these systems provide glenoid exposure problems.

What is thus needed in view of the above is a joint prosthesis that allows adjustment of the angular position of the head of the joint without utilizing a separate fastener or locking device to fix the position of the head.

What is thus further needed is a joint prosthesis that allows easy adjustment and locking of the angle of the head during surgery.

What is thus even further needed is a joint prosthesis that allows adjustability of the joint head after final implanting of a mating joint prosthesis stem.

SUMMARY

A joint prosthesis, as a replacement for a ball and socket type joint, has a head that allows for infinite dialability and/or angular orientation with respect to an implanted stem, particularly during a procedure for implanting the prosthesis. The angular orientation is positionable and fixed or locked in a set position without utilizing external or separate fasteners. A conjoining member associated with the prosthesis stem receives the head and allows for the positioning thereof. The conjoining member is fixed in position through expansion of the conjoining member to produce a friction fit (wedging) of the conjoining member within a receiving socket of the stem. Expansion of the conjoining member is achieved through coupling interaction of a stem of the head with the conjoining member.

The joint prosthesis provides infinitely adjustable three-dimensional angular positioning (i.e. medial to lateral and posterior to anterior) and locking of the joint head with respect to the implanted humeral stem thereof. An expandable spheroid rotatably retained in a socket of the joint stem, has an internal taper that receives a tapered stem or neck of the head. The bore allows reception of the stem (head) for thereafter setting the angular position of the head. Upon compaction of the stem (head) into the bore of the spheroid, the respective stem and bore tapers cause the spheroid to expand providing a wedging or friction fit of the spheroid in the socket. The fixed orientation of the spheroid determines the fixed orientation of the head.

In one exemplary form, the subject invention is a joint prosthesis. The joint prosthesis includes a conjoining member, a joint stem implantable into a bone, and a joint head. The conjoining member is configured to receive an expander whereby the conjoining member is fixed in angular orientation with respect to the joint stem through expansion of the conjoining member. The joint stem is implantable into a bone and has a concavity therein configured to receive the conjoining member. The conjoining member is free to swivel within the concavity in an unexpanded state but stationary within the concavity in an expanded state. The joint head has an articulation surface on one side thereof and carries the expander on another side thereof. The expander is received by the conjoining member whereby in an uncompacted state of the expansion member relative to the conjoining member, the conjoining member is in the unexpanded state and the joint head is therefore adjustably positionable in a plurality of medial-lateral and anterior-posterior orientations, and in a compacted state of the expander relative to the conjoining member, the conjoining member is in the expanded state whereby conjoining member and the joint head are fixed in angular orientation The conjoining member preferably has several expansion members that outwardly expand upon compaction.

BRIEF DESCRIPTION OF THE DRAWINGS

In the drawings.

Corresponding reference characters indicate corresponding parts throughout the several views. Like reference characters tend to indicate like parts throughout the several views.

Figure 1:
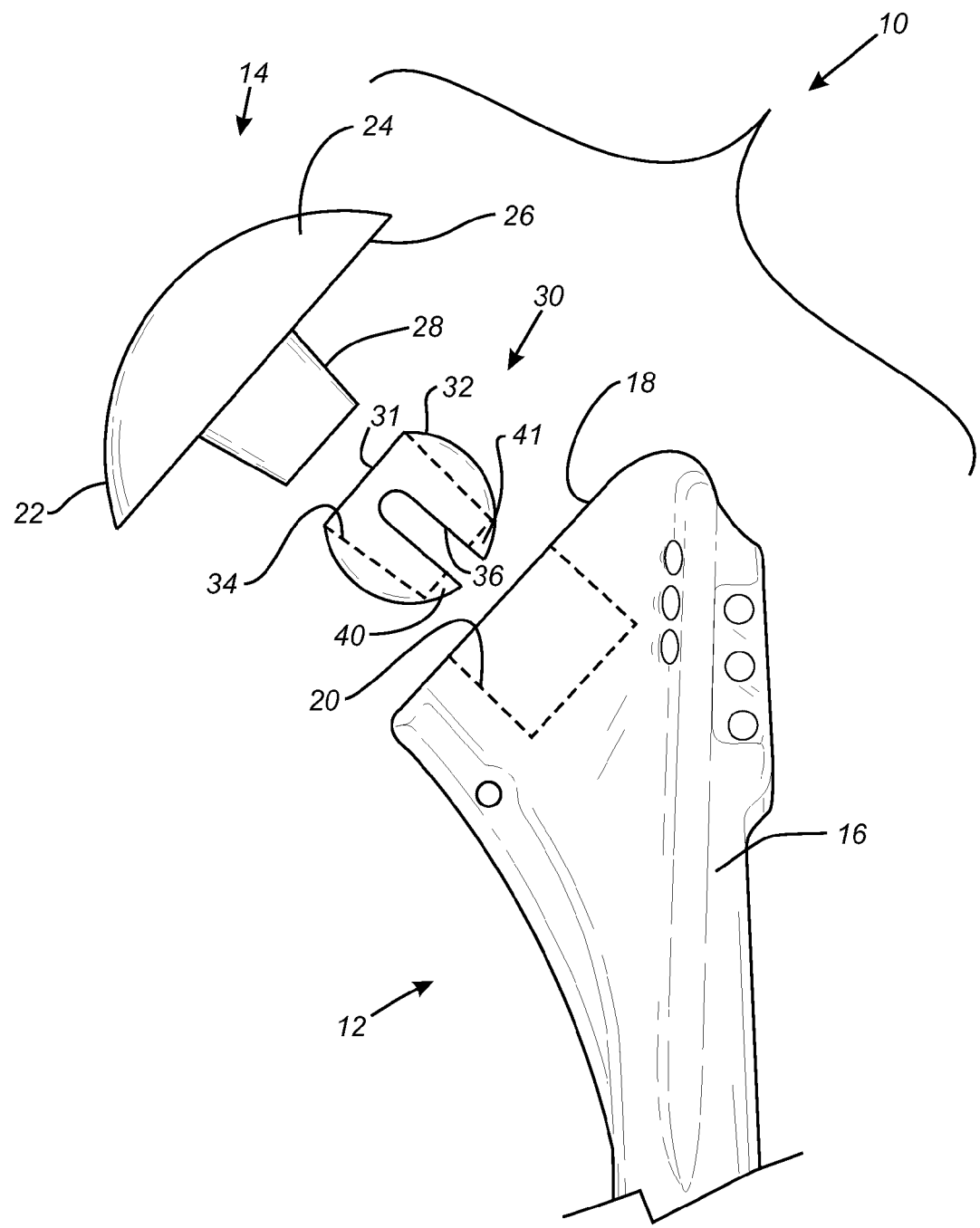
FIG. 1 is an exploded side perspective view of an exemplary shoulder prosthesis incorporating the features of the subject invention in accordance with the present principles.

DESCRIPTION OF THE PREFERRED
EMBODIMENT(S)

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1, there is depicted an exemplary embodiment of a joint prosthesis, generally designated 10, fashioned in accordance with the principles of the subject invention. The exemplary joint prosthesis 10 is designed to replicate a natural ball and socket type joint of a patient. The joint prosthesis 10 is illustrated in the figures and described herein as a shoulder prosthesis. It should be appreciated that the principles of the subject invention are applicable to various types of joint prostheses other than shoulder prostheses. Thus, while the principles of the subject invention are embodied in the figures as a shoulder prosthesis, the subject invention may be used in other types of prosthetic joints.

The shoulder prosthesis 10 includes a humeral component or stem 12, a humeral head or head component 14, and a conjoining member 30. The humeral stem 12 is adapted, operative and/or configured to be implanted into a surgically prepared humerus. The conjoining member 30 is adapted, operative and/or configured to be received by or on the stem 12. The head 14 is adapted, operative and/or configured to be received by or on the conjoining member 30. The conjoining member 30 and the head 14 are angularly positionable relative to the stem 12.

The conjoining member 30 is generally free to swivel, rotate and/or angularly move relative to the stem 12 when the conjoining member 30 is in an unlocked state and is constrained from movement (i.e. stationary) relative to the stem 12 when the conjoining member 30 is in a locked state. The conjoining member 30 carries the head 14 and thus provides swiveling, rotation and/or angular movement of the head 14 relative to the stem 12 in an unlocked state (i.e. allows angular positioning or orientation of the head), and constrains the head 14 from movement (i.e. stationary) relative to the stem 12 in a locked state (i.e. sets or fixes the angular position or orientation thereof).

In accordance with an aspect of the subject invention, the conjoining member 30 is constrained from movement (i.e. locked) with respect to the stem 12 without the need for separate and/or external locking mechanisms. The conjoining member 30 is locked via a friction fit or a wedging of the conjoining member 30 to the stem 12. This thus locks the angular orientation of the head 14.

The stem 12 is defined by a body 16 that is fashioned from a suitable and preferably fashioned from a suitable and preferably known implantable material such as a metal, plastic, composite, ceramic or the like. The body 16 has a distal portion (not shown) and a proximate portion that includes a flat upper surface 18. A bore, socket, recess, concavity or the like 20 (collectively, socket). Is disposed in the body 16 from the surface 18. In the shoulder prosthesis embodiment 10, the socket 20 is cylindrical in shape and thus has a given diameter and depth. The dimensions of the cylindrical socket 20 are related to the dimensions of the conjoining member 30 as discussed below. In general summation, the cylindrical socket 20 has a depth and a diameter configured to receive the conjoining member, allow angular movement (i.e. rotation, swiveling or the like) of the conjoining member 30 therein, and allow the conjoining member 30 to be fixed, constrained or the like (i.e. stationary) in angular position or orientation relative to the stem 12. Other concavity configurations are contemplated, one of which is shown with respect to the prosthesis embodiment of FIG. 6. The stem 12 is thus implantable into a humerus of a patient (not shown) in a known manner such that the surface 18 is exposed.

The conjoining member 30 is embodied in the exemplary embodiment 10 as a spheroid body 32 having a flat or flat surface 31. The spheroid body 32 is fashioned from a suitable implantable material such as is known in the art, the implantable material being compatible with the material of the stem 12 and/or concavity 20. The body 32 is sized to be received in the socket 20 of the humeral stem 12. Particularly, the diameter of the spheroid body 32 can be slightly less, slightly more, or equal to the diameter of the socket 20, while the height of the spheroid body 32 (from the surface 31 to the tip thereof) is the same or slightly less than the depth of the concavity 20.

The conjoining member 30 includes a bore 34 therein that axially extends from the surface 31 thereof. The bore 34 is defined by a sidewall that tapers inwardly along the axis of the spheroid body 32. Particularly, the sidewall defining the bore 34 radially diminishes or decreases (i.e. the sidewall reduces in diameter) axially from the opening of the bore 34 at the surface 31. The bore 34 may be considered frusto-conical in shape.

Figure 3:
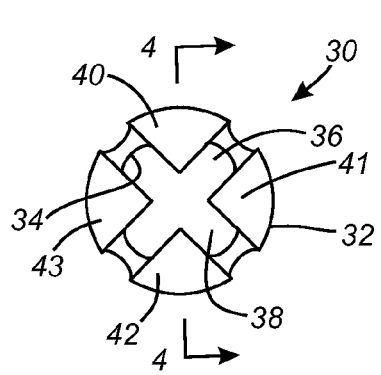
FIG. 3 is an enlarged bottom plan view of the conjoining member of the exemplary shoulder prosthesis of FIG. 1.
Figure 4:
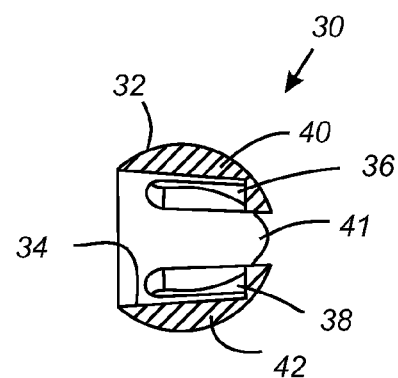
FIG. 4 is a sectional view of the conjoining member of FIG. 3 taken along line 4-4 thereof.

The conjoining member 30 is also configured, adapted and/or operative to expand. Referring additionally to FIGS. 3 and 4, the conjoining member 30 is depicted in greater detail. In addition to the tapered bore 34, the fixation member 30 has one or more slits or slots 36 defining a plurality of fingers, expansion members or the like labeled 40, 41, 42, and 43. It should be appreciated that the number of slots and/or expansion members are variable. Likewise, the orientation of the slots and/or fingers is subject to modification.

As seen in the figures, the expansion members 40, 41, 42, 43 each have an inner surface that is or is adjacent to the sidewall of the bore 34. Receipt of an expander of a given diameter and/or of a sufficient depth in the bore 34 causes the radial expansion of the expansion members. Radial displacement of the expansion members causes the fixation member 30 to be wedged or friction fit in the concavity 20 of the stem. This friction fit or wedging prevents or constrains the conjoining member 30 from movement within the concavity 20 (i.e. is locked or fixed).

Figure 2:
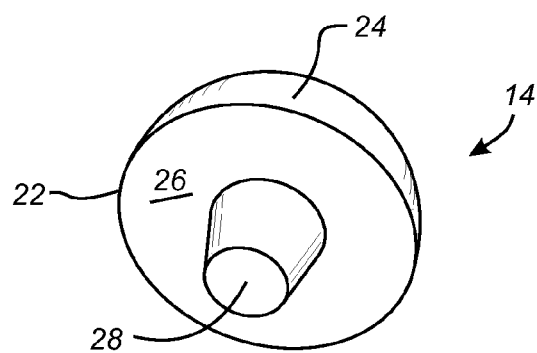
FIG. 2 is a bottom perspective view of the head portion of the exemplary shoulder prosthesis of FIG. 1.

Referring back to FIG. 1, the head 14 is adapted, configured and/or operative to be received on or in the conjoining member 30 or vice versa. With additional reference to FIG. 2, the head 14 is defined by a body 22 that is fashioned from a suitable material in like manner to the stem 12 and the conjoining member 30. The body 22 has an articulation surface 24 that is adapted, configured and/or operative to be received in a glenoid (not shown) of the patient. The body 22 also defines an underside 26 from which depends or on which is disposed an expander or neck 28 (collectively, expander). The expander 28 is defined by a tapered sidewall that may be considered frusto-conical in shape. The diameter of the expander at most points is preferably larger than the diameter of the bore 34 of the conjoining member 30.

The expander 28 is received in the bore 34 of the conjoining member 30. The expander 28 is sized to be initially received in the bore 34 without causing expansion of the conjoining member 30 (i.e. an unlocked or unexpanded state). Thus, the head 14 may be coupled to the stem 12 via the conjoining member 30 while allowing the head 14 and conjoining member 30 to swivel, rotate, and/or angularly move relative to the stem 12. Upon further axial movement of the head 14 (and thus the expander 38) into the bore 34, the conjoining member 30 is cause to expand within the concavity 20 of the stem 12. This is usually accomplished by compaction of the head 14 onto the conjoining member 30. Expansion of the conjoining member 30 is particularly the expansion of the expansion members 40, 41, 42, 43 that have been spread by the expander 28.

Figure 5:
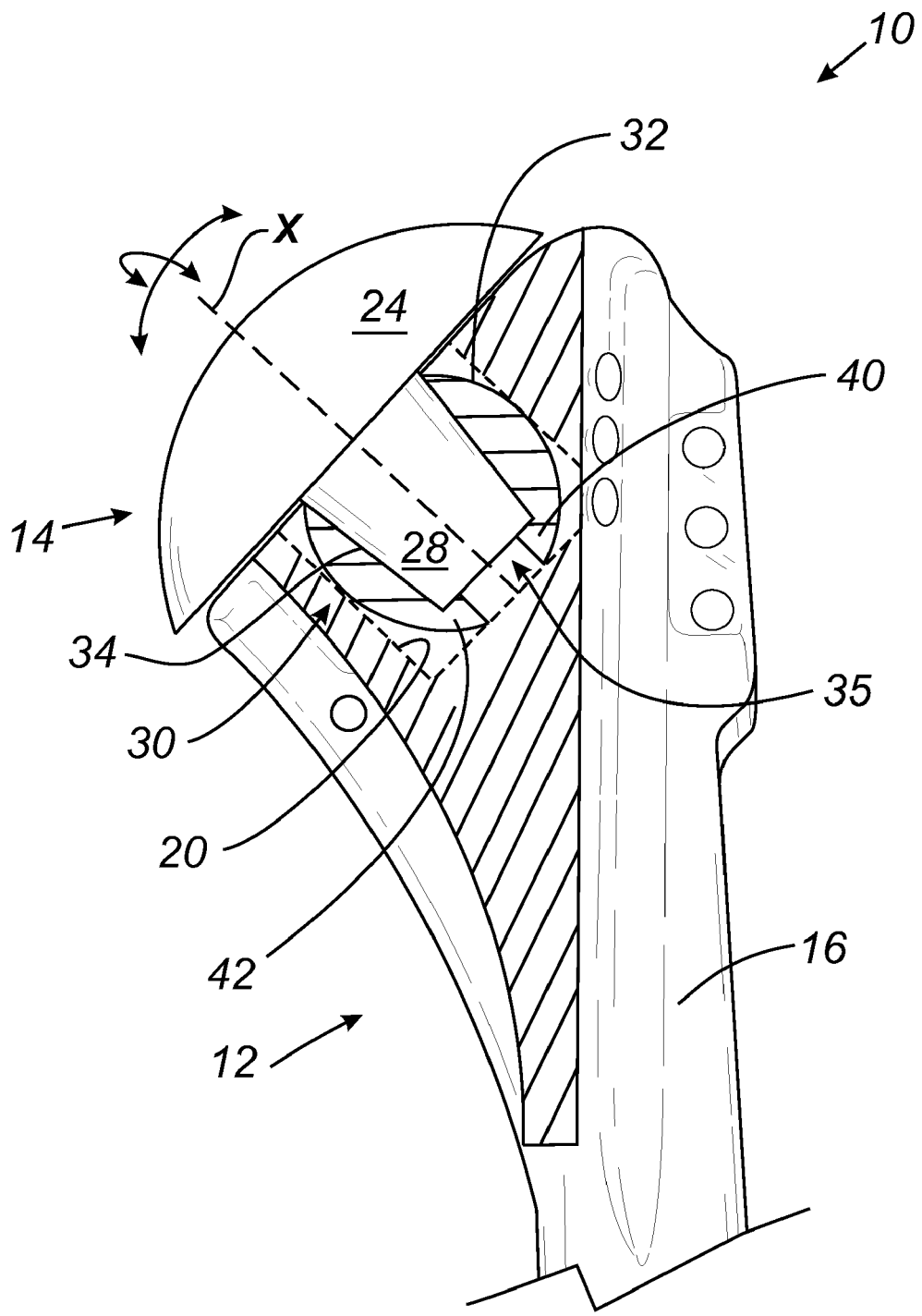
FIG. 5 is a side, partial sectional view of the exemplary shoulder prosthesis of FIG. 1 in an assembled (compacted) state.

In FIG. 5, the shoulder prosthesis 10 is depicted in an assembled state as it would typically be after implantation. The taper walls of 28 contact the bore walls 34 in the locked position causing radial expansion of the expansion members 40, 41, 42, 43 (of which expansion members 40 and 42 are seen). Radial expansion has occurred as evidence by the widened gap 35. Moreover, while the head 14 is shown fully compacted in the conjoining member 30 and thus the conjoining member 30 is expanded and locked from movement, it should be appreciated that the conjoining member 30 in an uncompacted state (unlocked and unexpanded) may be positioned such that the head 14 is infinitely angularly positionable or oriented about the axis "X" as represented by the arrows.

In the uncompacted state, the neck 28 does not fully seat or extend into the bore 34 (as it would be when the bottom of the neck 28 reaches, bottoms out, or is proximate to the bottom of the bore 34). In this initial position or state, the head is angularly positionable since the expansion members 40-43 are not expanded by the neck 28.

Figure 6:
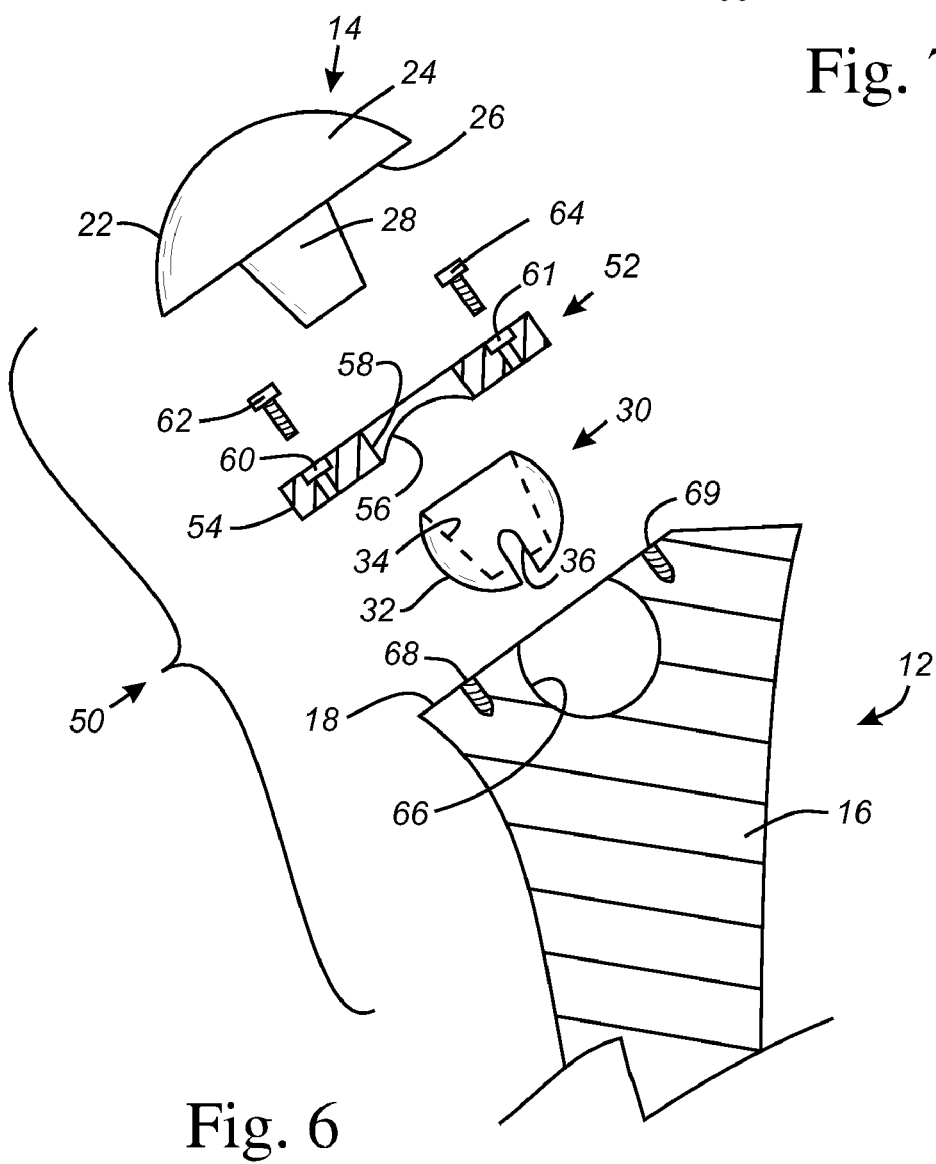
FIG. 6 is another exemplary embodiment of a shoulder prosthesis incorporating the features of the subject invention in accordance with the present principles.

Referring now to FIG. 6, there is depicted another exemplary embodiment of a joint prosthesis, generally designated 50, in accordance with the principles of the subject invention. The joint prosthesis 50 is again, a shoulder prosthesis. The shoulder prosthesis 50 includes the stem 12 defined by the body 16. The top surface 18, however, has a spheroid concavity 66 therein that is essentially configured in like shape as the conjoining member 30, but slightly larger to allow the conjoining member 30 to rotate therein in the same manner as that of the embodiment of FIG. 1. The spheroid concavity 66 is further sized to allow the conjoining member 30 to radially expand and become wedged or friction fit into the concavity 66 wherein the conjoining member is constrained from movement.

While the conjoining member (spheroid translating member, or fixation member) receives the head 14 defined by the body 22 having the neck 28 in like manner to the prosthesis 10 of FIG. 1, the shoulder prosthesis 50 of FIG. 6 includes a plate 52. The plate 52 is disposed between the head 14 and the conjoining member 30 and serves to retain the conjoining member 30 in the spheroid concavity 66.

Figure 7:
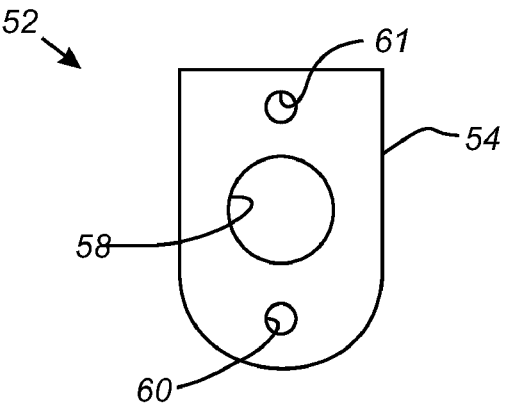
FIG. 7 is a top plan view of the retaining member of the exemplary shoulder prosthesis of FIG. 6.

FIG. 7 is a top view of the retention plate 52. The plate 52 is defined by a body 54 that is shaped to substantially conform in configuration to the surface 18 of the stem 12 and is fashioned from a suitable implantable material. The body 54 includes a neck opening 58 through which the expander or neck 28 of the head 14 extends for coupling with the bore 34 of the conjoining member 30. First and second fastener bores 60 and 61 are provided adjacent opposite sides of the neck bore 58. The bores 60 and 61 are configured as best seen in FIG. 6, in a countersunk manner to receive the screws 62 and 64 therethrough and allow the heads thereof to be flush with the surface of the plate 54.

The plate 54 includes an arcuate or semi-spheroid surface 56 that allow the conjoining member 30 to angularly move when the plate 54 is affixed to the surface 18 of the stem 12. The bore 58 is sized to allow the neck or expander 28 to extend therethrough and change in angular position or orientation as the head 14 moves in angular position or orientation during the unexpanded/uncompacted state when an appropriate angular orientation of the head 14 is being determined.

While not shown therewith, the embodiment of FIG. 1 may use a retention plate as necessary. Likewise, the embodiment of FIG. 6 may not utilize the retention plate. Many configurations are contemplated.

Implanting the Prosthesis

Figure 8:
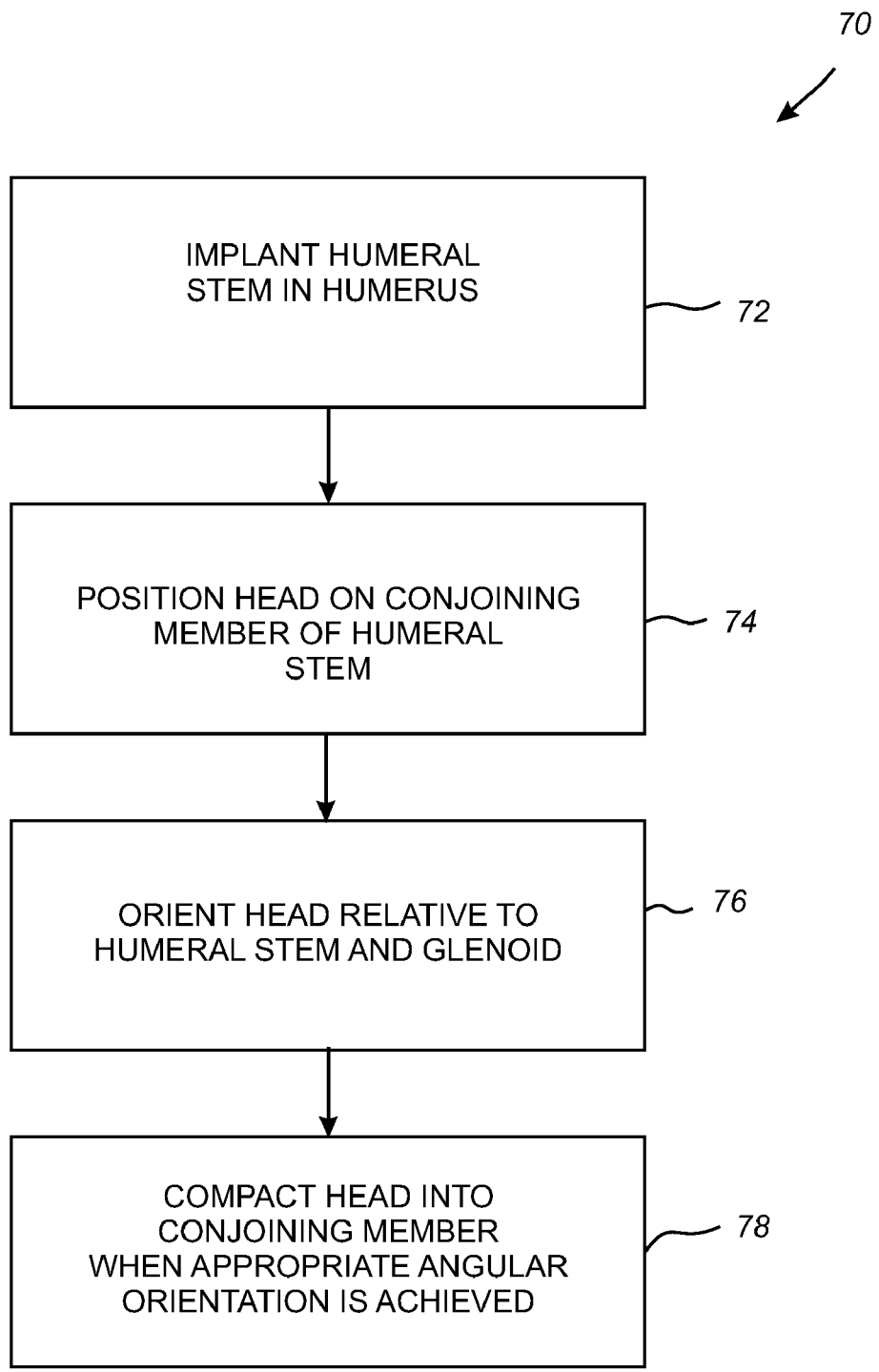
FIG. 8 is a flowchart of an exemplary manner of use of the subject invention.

A manner of implanting an embodiment of the subject invention will now be described, particularly in conjunction with the flowchart, generally designated 70, of FIG. 8. In step or block 72, the humeral stem 12 is implanted into the humerus of a patient. The humerus is initially prepared as is necessary and/or typical for implanting the humeral stem 12. This includes resecting a portion of the humerus. Once the humeral stem 12 has been implanted, in step 74, the head or head component 14 is placed on the conjoining member. Particularly, the neck or expander 28 of the head 14 is placed in the bore 34 of the conjoining member 30 such that the head 14 is carried by the conjoining member 30. At this point, the conjoining member 30 is in an unexpanded state (i.e. the head 14 has not been compacted into the conjoining member 30) and thus the conjoining member 30 is free to move (rotate, swivel or the like) within the concavity 20 of the stem 12 thus moving the head 14 as well.

In step 76, the head 14 is positioned into an appropriate angular orientation (i.e. the head 14 and conjoining member 30 are swiveled into the appropriate position). The surgeon determines the appropriate angular position. In step 76, the angular position of the head 14 is fixed, locked or set by compacting the head 14 onto the conjoining member 30 (i.e. by causing the conjoining member 30 to expand). This sets the angular position of the head.

There is a plurality of advantages of the subject invention arising from the various features of the shoulder prosthesis described herein. It will be noted that alternative embodiments of the shoulder prosthesis of the subject invention may not include all of the features described yet still benefit from at least some of the advantages of such features. Those of ordinary skill in the art may readily devise their own implementations of a shoulder prosthesis that incorporate one or more of the features of the subject invention and fall within the spirit and scope of the subject invention.

What is claimed is:

1. A joint prosthesis comprising:
   a joint stem implantable into a bone and having a concavity therein;
   a conjoining member having a spheroidal body which, when disposed in the concavity, is free to swivel within the concavity in an unexpanded state but stationary within the concavity in an expanded state, the conjoining member having a bore formed in it which can receive an expander by means of which the conjoining member can be expanded to lock the conjoining member in a selected angular orientation; and
   a joint head having an articulation surface on one side thereof, the expander being tapered,
   wherein the bore in the conjoining member is inwardly tapered, and the joint head carries the expander on its underside opposite to the articulation surface, the expander being tapered inwardly towards its free end so that it can be received in the bore in the conjoining member so that, (i) the conjoining member is in the unexpanded state while the expander is not compacted relative to the conjoining member, allowing the joint head to be adjustably positionable in a plurality of medial-lateral and anterior-posterior orientations, and (ii) the conjoining member and the joint head can be fixed in a selected angular orientation by compacting the expander relative to the conjoining member to cause the conjoining member to expand.

2. The joint prosthesis of claim 1, in which the conjoining member is radially expandable.

3. The joint prosthesis of claim 2, in which the conjoining member comprises a slotted spheroid.

4. The joint prosthesis of claim 1, in which the sidewall of the expander has a diameter that is greater than a diameter of the sidewall of the bore.

5. The joint prosthesis of claim 1, in which the concavity comprises a cylindrical socket.

6. The joint prosthesis of claim 1, in which the concavity comprises a spheroid concavity.

7. The joint prosthesis of claim 1, which is a shoulder prosthesis in which the joint stem is a humeral stem which is configured to be implanted into a resected humerus of a patient.

* * * * *